United States Patent [19]

Reif et al.

[11] Patent Number: 4,811,847
[45] Date of Patent: Mar. 14, 1989

[54] URINARY CATHETER PACKAGE

[76] Inventors: Thomas H. Reif, 5213 Greencroft Dr., Dayton, Ohio 45426; Louis E. Warnken, 197 Lindall Dr., Germantown, Ohio 45327; Roy A. Snyder, 8705 Cheshire Ct., Jessup, Md. 20794

[21] Appl. No.: 167,360

[22] Filed: Mar. 14, 1988

[51] Int. Cl.[4] ............................................. B65D 83/10
[52] U.S. Cl. .................................. 206/571; 206/364; 206/365; 206/210; 206/213; 206/278
[58] Field of Search ............... 206/571, 364, 365, 366, 206/210, 213, 278

[56] References Cited

U.S. PATENT DOCUMENTS

| | | |
|---|---|---|
| 2,009,825 | 7/1985 | Wappler . |
| 2,856,932 | 10/1958 | Griffitts . |
| 3,154,080 | 10/1964 | Rowan et al. . |
| 3,169,527 | 2/1965 | Sheridan . |
| 3,235,069 | 2/1966 | Bennett et al. . |
| 3,345,988 | 10/1967 | Vitello . |
| 3,421,509 | 1/1969 | Fiore . |
| 3,556,294 | 1/1971 | Walck et al. . |
| 3,606,889 | 9/1971 | Arblaster . |
| 3,648,704 | 3/1972 | Jackson . |
| 3,683,928 | 8/1972 | Kuntz . |
| 3,750,875 | 8/1973 | Juster . |
| 3,851,649 | 12/1974 | Villari . |
| 3,853,130 | 12/1974 | Sheridan . |
| 3,854,483 | 12/1974 | Powers . |
| 3,861,395 | 1/1975 | Taniguchi . |
| 3,894,540 | 7/1975 | Bonner, Jr. . |
| 3,898,993 | 8/1975 | Taniguchi . |
| 3,934,721 | 1/1976 | Juster et al. . |
| 3,967,728 | 7/1976 | Gordon et al. . |
| 4,140,127 | 2/1979 | Cianci et al. . |
| 4,160,505 | 7/1979 | Rauschenberger . |
| 4,178,735 | 12/1979 | Jackson . |
| 4,226,328 | 10/1980 | Beddow . |
| 4,230,115 | 10/1980 | Walz et al. . |
| 4,327,723 | 5/1982 | Frankhouser . |
| 4,327,735 | 5/1982 | Hampson . |
| 4,539,234 | 9/1985 | Sakamoto et al. . |

*Primary Examiner*—Joseph Man-Fu Moy
*Attorney, Agent, or Firm*—Becker & Becker, Inc.

[57] ABSTRACT

A package for an urinary catheter consists of a generally rectangular tray with an open top, to which a peel-back cover is bonded, containing a catheter assembly, a syringe prefilled with bacteriostatic water, and two gloves. The catheter assembly is designed such that a urinary catheter may be simply and efficiently placed into the bladder under sterile conditions. The catheter assembly consists of a heat shrunk seal to hold the end cap, three intermediate caps with antiseptic soaked sponge tips bonded to the ends, and the tube-like guide in proximity therewith. The catheter passes through the guide after removal of the heat shrunk seal and the systematic removal and utilization of the end cap and the three intermediate caps. A protective shroud encloses the distal end of the catheter, as it is bonded to the guide. A biocompatible lubricant is contained between the third intermediate cap and the guide.

12 Claims, 3 Drawing Sheets

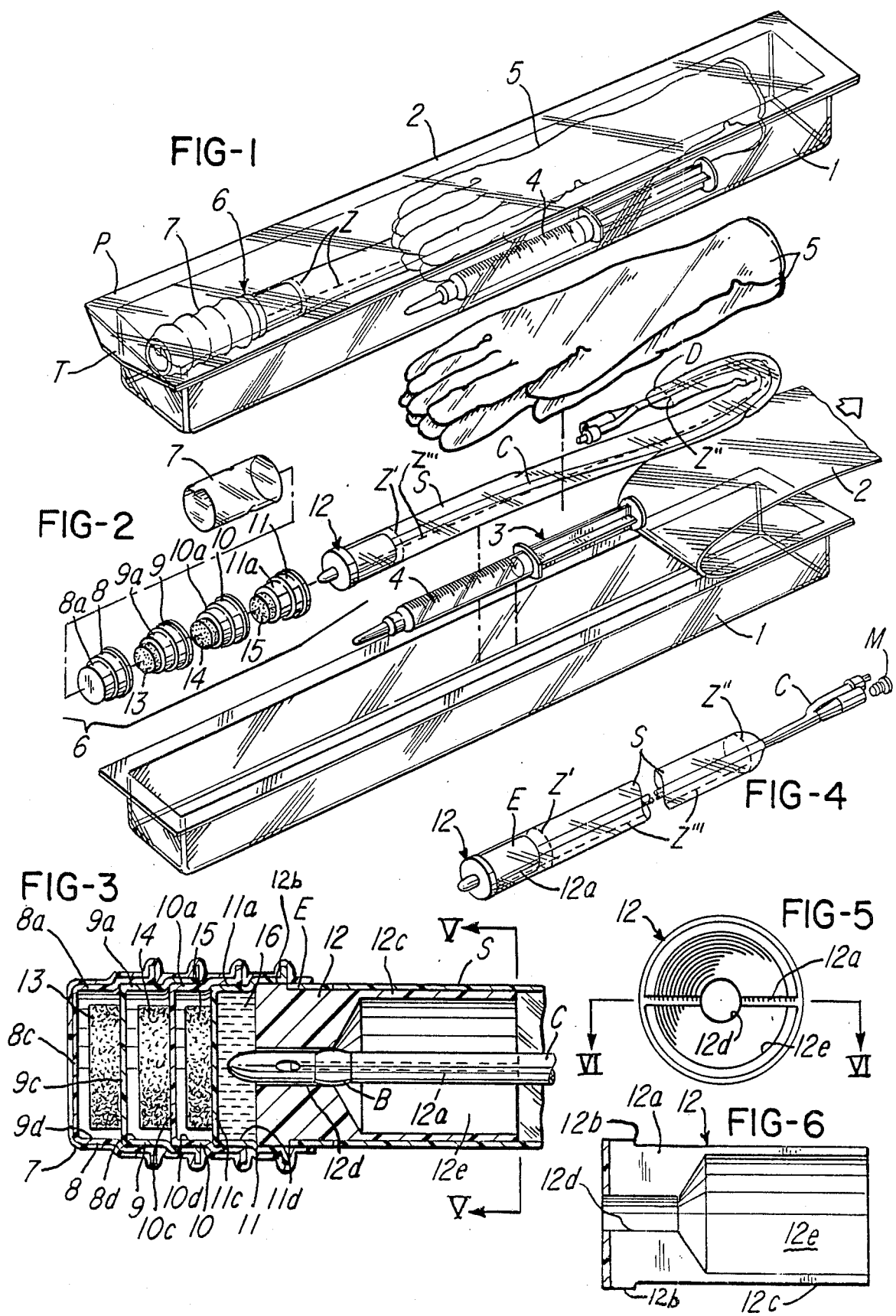

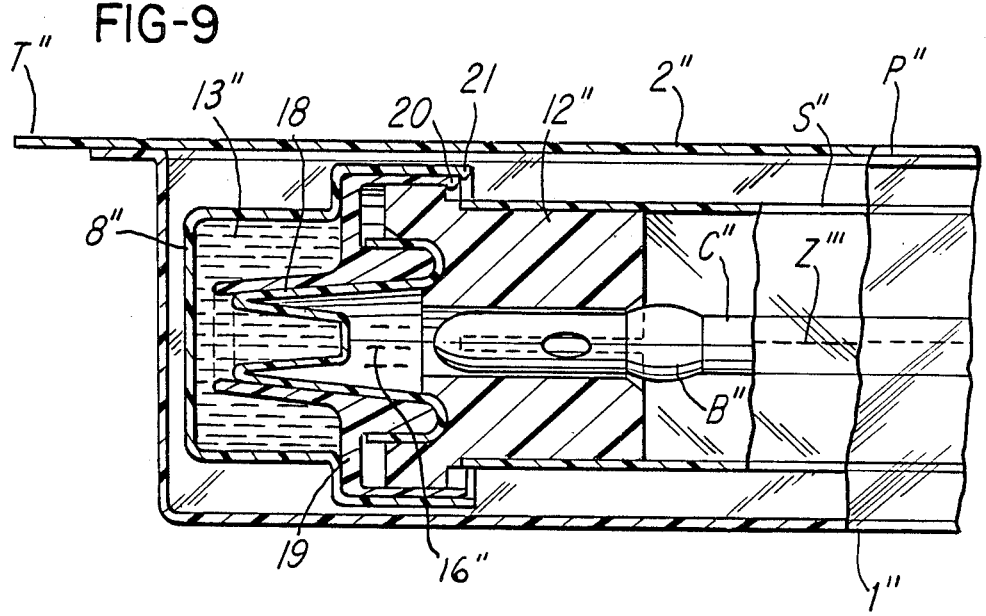

URINARY CATHETER PACKAGE

BACKGROUND OF THE INVENTION

1. Field of the Invention

The present invention pertains to a special receptacle or package, and, more particularly, pertains to a surgical or therapeutic type of special receptacle or package.

2. Description of the Prior Art

There are numerous reasons that persons, both hospitalized and non-hospitalized, are unable to evacuate or control the evacuation of their bladders. Examples include persons undergoing general anesthesia prior to surgery, nursing home residents who are suffering from dementia, and persons who have received lower spinal cord injuries.

Typically, these persons require the installation of an indwelling urinary catheter, usually a Foley catheter, into their bladder via their urethra. Current medical practice suggests the following method of insertion by properly trained medical personnel.

First, the necessary equipment is assembled. This may be performed by obtaining a pre-assembled kit (or kits) or by obtaining each of required components separately. Whatever the case, however, the required equipment is essentially as follows: a sterile towel, two sterile gloves, a pair of sterile forceps, three sterile swabs, a predetermined quantity of sterile antiseptic solution (usually iodine solution), a predetermined quantity of sterile lubricant, a sterile syringe, and a predetermined quantity of sterile water.

Second, a sterile field is established, usually with the sterile towel. The rest of the necessary equipment is then made ready or placed in the sterile field. There are several methods of completing this step, depending on whether or not the necessary equipment came in a pre-assembled kit (kits) or not.

Next, the gloved (both hands) inserter exposes the distal urethral ostia of the insertee by manipulating the external genitalia of the insertee with one hand, referred to as the left hand for the purposes of this discussion. The left hand is now considered non-sterile.

The inserter next picks up the forceps with the right hand and then grasps one of the swabs with the forceps. The swab is then dipped into the antiseptic solution and it is then used to cleanse the urethral ostia of the insertee. The first swab is then discarded away from the sterile field and the process is then repeated with the other two swabs. The forceps are then also discarded away from the sterile field by the inserter.

The still sterile right hand of the inserter is then used to grasp to catheter and to apply the lubricant to the proximal end of the catheter. The lubricated catheter is then advanced into the urethral ostia of the insertee until urine flows from the distal end of the catheter. The inserter may at this time remove the left hand from the external genitalia of the insertee. Both hands of the inserter may now be used to inflate the balloon tip of the catheter, to connect the distal end of the catheter to the proximal end of the drainage tube, and to clean up the residue of the procedure.

In summary, there are several disadvantages to the current methods and procedures for the insertion of indwelling urinary catheters. Considerable equipment is required and there may be considerable redundancy in packaging, depending upon the exact nature of the pre-assembled packages for individual or separate kit items utilized. Further, considerable attention to detail and time is required to properly perform the procedure.

The package for an urinary catheter of the present invention overcomes these deficiencies of the prior art and provides a unitary package that significantly improves the methods and procedures for the insertion of indwelling urinary catheters. This unitary package reduces and consolidates the amount of equipment required for the insertion of the urinary catheter. Thus, there is less cost due to elimination of redundancy in the packaging, a reduction in the complexity of the procedure, and a less time consuming and safer insertion procedure results therefrom.

SUMMARY OF THE INVENTION

The general purpose of the present invention is to disclose a unitary and compact package for an urinary catheter which may be used by trained medical personnel to install an indwelling urinary catheter. The unitary package for an urinary catheter is sealed to hold sterilized items therein progressively utilize, including a tube-like guide, which together with a protective shroud encloses a urinary catheter.

According to the preferred embodiment of the present invention, the tube-like guide is joined to a series of four nesting caps. The inner three caps have antiseptic soaked sponge tips secured to the caps, while the innermost cap contains lubricant. All four caps are easily removed upon breaking and peeling away a heat shrunk package seal. All of these elements are contained in a rectangular box-like tray of plastic material with a peel-back cover thereon. Also, gloves and a prefilled syringe are included in the tray.

A significant aspect and feature of the present invention is the reduction in the number of pieces of equipment necessary for the insertion of the catheter, making the package more cost effective. This is because of the functional consolidation of several of the necessary pieces of equipment into the package.

Another significant aspect and feature of the present invention is compact size of the package, making the package easier to handle and store. This also results from the functions consolidation of several of the necessary pieces if equipment into the package.

A further significant aspect and feature of the present invention is the reduction in the complexity of catheter installation procedure. This is because of the reduction in the number of pieces of equipment necessary for the insertion of the catheter.

An additional significant aspect and feature of the present invention is the reduction in the time of the catheter installation procedure. This results from the reduction in the complexity of catheter installation procedure. The patient is the ultimate beneficiary, having received a more cost effective, less complicated, less time consuming and safer procedure.

Having thus described the present invention, it is a principal object hereof to provide a package for an urinary catheter.

An object of the present invention is to provide a package for an urinary catheter which provides for the safe and effective sterile installation of a urinary catheter.

Another object of the present invention is to provide a package for an urinary catheter that can be stocked as medical or surgical supplies in different sizes and configurations with regard to length, diameters, and catheter types.

A further object of the present invention is to provide a package for an urinary catheter which provides for the safe and effective storage of a urinary catheter.

BRIEF DESCRIPTION OF THE DRAWINGS

These objects and other objects and advantages of the present invention will appear more clearly from the following specification in conjunction with the accompanying drawings, in which like reference numerals designate like parts throughout the figures thereof and wherein:

FIG. 1 depicts a perspective view of the package for an urinary catheter unitarily encased by a heat shrunk seal prior to disassembly;

FIG. 2 depicts a perspective and exploded view of parts in the catheter assembly after removal of the heat shrunk seal therefrom;

FIG. 3 depicts an enlarged fragmentary cross-sectional elevated view of a guide end portion having features including successive nesting caps carried by the guide and arranged in accordance with the present invention;

FIG. 4 is a fragmentary perspective view of the guide after removal of successively nesting caps therefrom;

FIG. 5 is a cross-sectional view taken in the direction of arrows along line V—V in FIG. 3;

FIG. 6 is a cross-sectional view taken in the direction of arrows along the VI—VI in FIG. 5;

FIG. 9 is a fragmentary cross sectional elevational view of a further alternative embodiment of the package for an urinary catheter having features according to the present invention.

DESCRIPTION OF THE PREFERRED EMBODIMENTS

Figure 7:
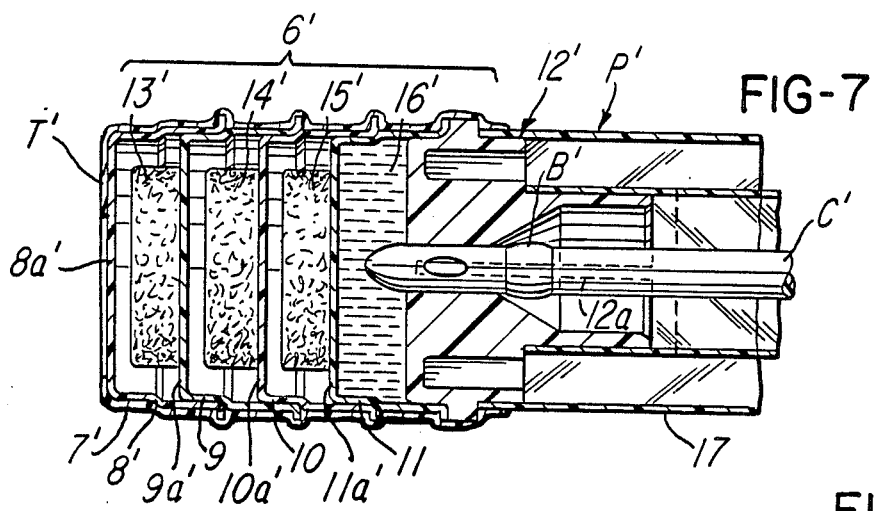
FIG. 7 depicts an enlarged fragmentary cross-sectional elevational view of an alternative embodiment of the package for an urinary catheter prior to disassembly and having features in accordance with the present invention.

FIG. 1 collectively depicts parts of a package P hermetically as a sealed unit for an urinary catheter prior to disassembly. A tray 1 of transparent or translucent plastic material such as a polyethylene container or enclosure means is shown bonded to a peel-back top cover 2 with a pull tab T of paper or plastic material for example. The tray 1 contains a syringe 3, prefilled with bacteriostatic water 4 therein, rubbery gloves 5, and the catheter end portion assembly 6 having a heat shrunk plastic seal 7 surrounding telescoped successive plastic cup-shaped cap members 8, 9, 10 and 11 of telescopically interfitted polyethylene plastic material for example.

FIG. 2 shows the parts of the package P in a perspective and exploded view after peeling away the heat shrunk top cover 2.

The catheter assembly is shown in cross-section in FIG. 3, removal of the outer heat shrunk seal 7 (FIG. 1) which mechanically fixes an end cap, three intermediate caps and a guide in predetermined proximity preventing damage to internal parts and serving as a sterile barrier. A cup-shaped end cap 8 having a closed end nests with respect to a closed end of a first intermediate cup-shaped cap 9, which in turn nests with respect to a closed end of a second intermediate cup-shaped cap 10, which in turn nests with respect to a closed end of a third intermediate cup-shaped cap 11, which finally nests with a guide 12 of solid plastic material such as polyethylene. Antiseptic soaked sponge tips 13, 14, 15 are bonded or secured adhesively, respectively to the closed ends of the three intermediate cup-shaped caps 9, 10, 11. A biocompatible lubricant 16 is enclosed between the third intermediate cup-shaped cap 11 and the guide 12 of plastic material. A urinary catheter C is partially enclosed by the guide 12 and a protective shroud S of plastic material, such as polyethylene. A proximal end E of the protective shroud S is bonded to the distal end of the guide 12c as shown in FIGS. 3 and 4. The distal end of the protective shroud is bonded to the distal end pf the catheter C. The protective shroud S is sealed bonded to the distal end of the catheter C.

FIGS. 5 and 6 depict the tube-like guide 12. The guide 12 has a slot 12a longitudinally thereof, whereby the guide 12 can be removed from the catheter C (FIGS. 2, 3 and 4) upon disassembly. A proximal outer surface 12b nest within the third intermediate cap 11 (FIGS. 3 and 6), while the distal outer surface 12c is dimensioned such that it can be bonded to the proximal end E of the protective shroud S (FIG. 2). The catheter C (FIGS. 2, 3 and 4) has a loose-running or alignment-with-play fit with the smaller inside diameter of the guide 12d (proximal end E). The larger inside diameter 12e (distal end D) is relieved for easy assembly and sparing or saving of plastic material as well as for weight reduction.

The end cap 8 and the intermediate caps 9, 10, 11 are made of plastic material having an identical configuration for nesting and production purposes. The caps are depicted in cross-section in FIG. 3 and perspective end view in FIG. 2. The caps have proximal outer surfaces 8a, 9a, 10a, 11a that are designed to nest into the distal inner diameters of the caps 8, 9, 10, 11 respectively. The caps have closed ends 8c, 9c, 10c, 11c that are flat to accommodate the bonding of the sponge tips 13, 14, 15 thereto (FIGS. 2 and 3). The caps have proximal inner diameters 8d, 9d, 10d, 11d that are equal to each other and adapted also to accommodate the sponge tips 13, 14, 15 therein (FIGS. 2 and 3).

Mode of Operation

The unitary package P for an urinary catheter C, prior to use, is shown in FIG. 1. To utilize the unitary package P, the peel-back cover 2 is removed from the container or tray 1. Although the contents are sterile, they may be handled or laid out on a non-sterile field or surface. The gloves 5 are put on or donned. The heat shrunk seal 7 is then removed from the catheter assembly 6 (FIGS. 1 and 2).

The gloved left hand is then used to expose the distal urethral ostia of the insertee. The catheter assembly is then picked up with the gloved (an added precaution) right hand. The end cap 8 is then removed with the thumb of the right hand or the free digits of the left hand. The first sterilized sponge tip 13 (FIGS. 2 and 3) of the first intermediate cap 9 is used to cleanse the urethral ostia. Next the first intermediate cap 9 is removed with the thumb of the right hand. The still sterilized sponge tip 14 of the second intermediate cap 10 is then exposed and it is used to again cleanse the urethral ostia. The second intermediate cap 10 is removed and the still sterilized sponge tip 15 of the third intermediate cap 11 is used to cleanse the urethral ostia for the third and final time.

The third intermediate cap 11 is removed with the thumb of the right hand. The left hand is still holding the external genitalia such that the now sterile distal urethral ostia is clearly exposed. The lubricant 16 soaked proximal end of the catheter C is now exposed and is placed into the urethra. The catheter C is advanced with the right hand through the protective shroud S and then is advanced until urine is seen in a distal end D of the protective shroud S.

At this stage of the procedure, the left hand may be removed from the genitalia. The gloves may be removed, if desired. The syringe 3 prefilled with bacteriostatic water 4 are then used to inflate a balloon B inside the catheter C. The syringe 3 is removed and the distal end D of the catheter C is connected to a urinary metering deivce M. The plastic shroud S is removed by tearing it along the proximal serration Z', the distal serration Z", and the longitudinal serration Z"'. The guide 12 is removed by breaking it at its slot 12a (FIGS. 5 and 6). The catheter C remains in the insertee, while all other materials are discarded.

Alternative Embodiment

Figure 8:
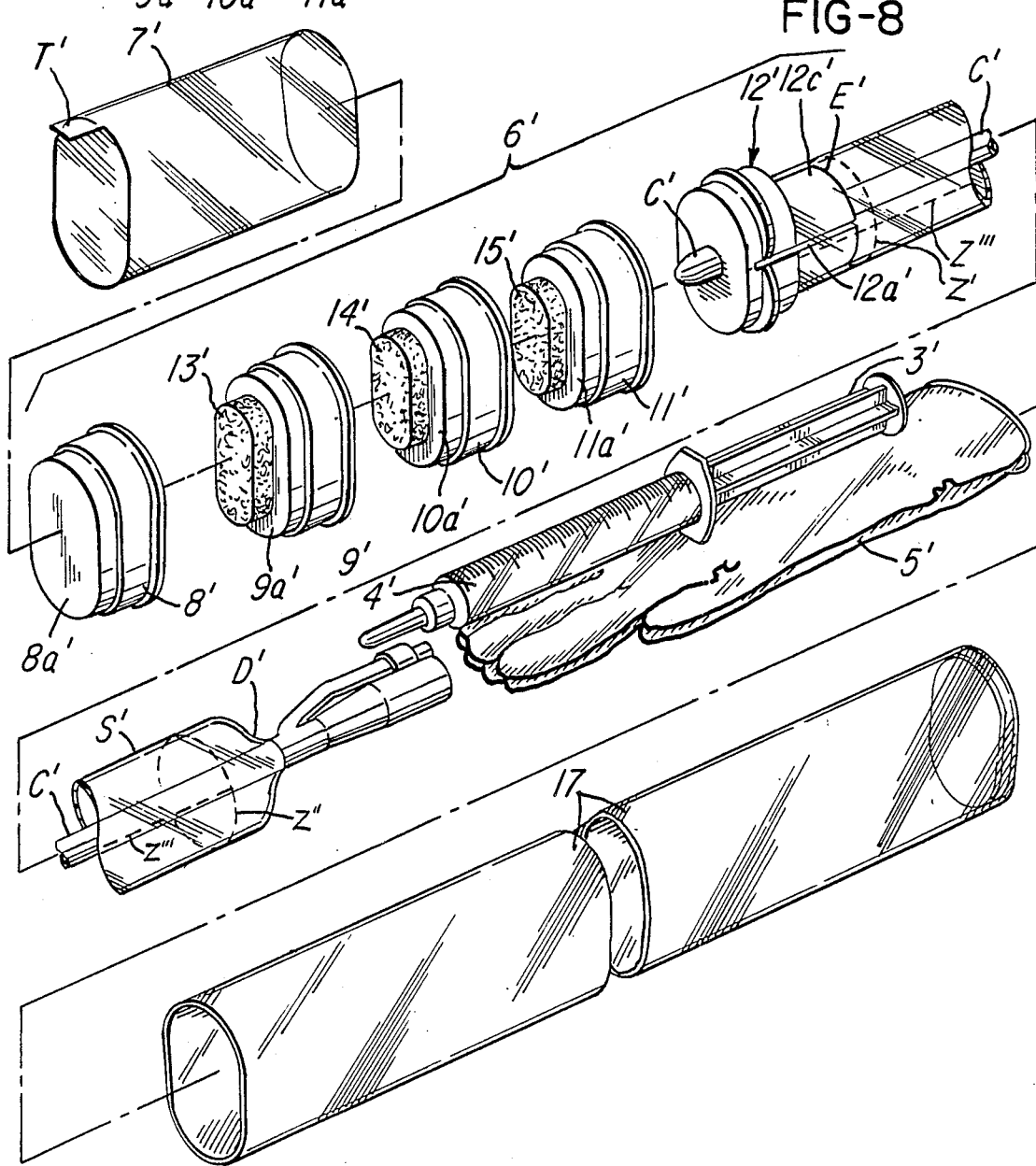
FIG. 8 depicts a perspective and exploded view of parts or items in catheter assembly of FIG. 7 and after removal of the heat shrunk seal therefrom.

FIGS. 7 and 8 depict an alternative embodiment of the package P' as an enclosure housing means for an urinary catheter C'. This embodiment differs from the preferred embodiment in that a tube-like body 17 of plastic material such as polyethylene is used as the enclosure means for housing the sterilized catheter assembly 6' as opposed to the tray 1 (FIG. 1). The body 17 joins the guide 12' as shown in FIG. 7. The caps 8', 9', 10', 11' as well as the sterilized sponge tips 13', 14' and 15' respectively, the guide 12', and the body 17 are elliptical in shape to facilitate handling and storage. Components or parts comparable to each other in the alternative embodiment of FIGS. 7 and 8 have primes added to the reference numerals thereof.

FIG. 9 depicts a second alternative embodiment of the package P" or an enclosure having means for an urinary catheter C". This embodiment differs from the preferred embodiment in that a single cup-shaped end cap 8", a urethral meatal guide 19, and a modified guide 12" replace the three nesting caps 8, 9, 10 and the guide 12 (FIG. 1). The modified guide 12" joins the urethral meatal guide 19, enclosing a diaphram 18. The end cap 8" joins the urethral meatal guide 19. Lubricant 16" lies between the diaphram 18 and the modified guide 12". Antiseptic solution 13" may be housed within the end cap 8". As the end cap 8" is removed, the urethral meatal guide 19 is inserted into the urethral meatus. The catheter C" is advanced through the modified guide 12" causing the diaphragm 18 to unroll into the urethra. The diaphragm is designed such that unrolling occurs instead of sliding, this prevents the contamination of the more sterile areas in the urethra by the less sterile areas. When the catheter C" is advanced a predetermined length, the diaphram 18 ruptures and the catheter C" can be easily advanced or used. Also provided are retaining lugs or protrusions 20 on guide 19 as well as retaining lugs or protrusions 21 on cap 8" as shown in FIG. 9. Components or parts comparable to each other in the alternative embodiment of FIG. 9 have double primes added to the reference numerals thereof.

The present invention is, of course, in no way restricted to the specific disclosure of the specification and drawings, but also encompasses any modifications within the scope of the appended claims.

What we claim is:

1. A unitary package sealed in sterilized condition for holding an urinary catheter and protective parts therewith comprising:

enclosure means including a seal having a pull-tab;

an end cap as one of the protective parts mounted telescopically relative to each other;

at least three intermediate (first, second, and third) caps each having closed proximal ends and having antiseptic soaked sponge tips carried thereon also as protective parts mounted telescopically and progressively relative to each other;

a tube-like guide having a distal end and having a covered proximal end telescopically fitted to one of said intermediate caps;

a urinary catheter having one end projecting axially through said guide;

a tube-like protective shroud for said urinary catheter;

a predetermined amount of biocompatible lubricant located adjacent to the covered end of said guide and having the one end of the catheter projecting axially through said guide also projecting into the lubricant;

a syringe containing a predetermined amount of bacteriostatic water and housed sterilized in said enclosure means;

sterilized gloves means housed in said enclosure means and a peel-back cover of said enclosure means;

said end cap joins in a telescopic fit onto said first intermediate cap;

said first intermediate cap joins in a telescopic fit onto said second intermediate cap;

said second intermediate cap joins in a telescopic fit onto said third intermediate cap;

said third intermediate cap joins in a telescopic fit onto proximal end of said guide;

said protective shroud being bonded to the distal end of said guide;

said antiseptic soaked sponge tips being secured to the proximal ends of said intermediate caps;

said lubricant being contained as located between said third intermediate cap and said guide;

said heat shrunk seal protectively covers and joins said end cap, three intermediate caps, and guide;

said enclosure means containing said heat shrunk seal, end cap, three intermediate caps having antiseptic soaked sponge tips, guide, urinary catheter, lubricant, protective shroud, glove means, and syringe so that the package may be disassembled in proper sequence progressively such that said urinary catheter may be inserted into the urinary tract under sterile conditions.

2. A package according to claim 1 wherein said heat shrunk seal mechanically fixes said end cap, three intermediate caps, and guide in predetermined proximity preventing damage to internal parts and serving as a sterile barrier.

3. A package according to claim 1 in which said enclosure means is a tray of plastic material having said peel-back cover thereon.

4. A package according to claim 1 in which said caps are cup-shaped.

5. A package according to claim 1 in which said enclosure means is a tube-like body of plastic material.

6. A package according to claim 1 in which said enclosure means is a tube-like body of plastic material having an elliptical shape in cross section to facilitate handling and storage.

7. A package according to claim 6 in which said caps, guide and sponge tips all also have an elliptical shape in cross section.

8. A package according to claim 1 in which said guide is made of plastic material having a slot longitudinally thereof to allow breaking apart of said guide for removal from the catheter.

9. A package according to claim 1 in which a balloon is provided inside the catheter and is inflatable via said syringe also collectively kept sterile therewith inside said enclosure means.

10. A package according to claim 1 in which said sponge tips are bonded to the proximal ends of said intermediate caps.

11. A unitary package sealed in sterilized condition for holding an urinary catheter and protective parts therewith comprising:
   enclosure means including a seal having a pull-tab;
   at least one intermediate cap having a closed proximal end and having antiseptic soaked sponge tip means carried thereon;
   a tube-like guide having a distal end and having a covered proximal end telescopically fitted to said intermediate cap;
   a urinary catheter having one end projecting axially through said guide;
   a tube-like protective shroud for said urinary catheter;
   a predetermined amount of biocompatible lubricant located adjacent to the covered end of said guide and having the one end of the catheter projecting axially through said guide also projecting into the lubricant;
   an end cap that joins in a telescopic fit onto said intermediate cap;
   said protective shroud being bonded to the distal end of said guide;
   said antiseptic soaked sponge tip means being secured to the proximal end of said intermediate cap;
   said lubricant being contained as located between said intermediate cap and said guide;
   said seal protectively covers and joins said end cap, intermediate cap, and guide;
   said enclosure means containing at least said seal, end cap, intermediate cap having antiseptic soaked sponge tip means, guide, urinary catheter, lubricant, protective shroud, and syringe so that the package may be disassembled in proper sequence progressively such that said urinary catheter may be inserted into the urinary tract under sterile conditions.

12. A package according to claim 11 with which a serration means is provided along said protective shroud removable thereby for access to the catheter.

* * * * *